United States Patent [19]
Kim

[11] Patent Number: 6,071,521
[45] Date of Patent: *Jun. 6, 2000

[54] PHARMACEUTICAL COMPOSITION HAVING AN ANTITUMOR ACTIVITY AND A PROCESS FOR PREPARATION THEREOF

[76] Inventor: Song Bae Kim, 192-11 Dukmyung-Dong, Yusung-Ku, Daejeon, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 08/520,505

[22] Filed: Aug. 28, 1995

Related U.S. Application Data

[63] Continuation of application No. 08/150,538, Nov. 10, 1993, abandoned, which is a continuation of application No. 07/867,076, Apr. 14, 1992, abandoned, which is a continuation of application No. 07/577,010, Sep. 4, 1990, abandoned.

[30] Foreign Application Priority Data

Sep. 4, 1989 [KR] Rep. of Korea ........................ 89-12750

[51] Int. Cl.$^7$ ................................................. A61K 35/78
[52] U.S. Cl. ........................................................ 424/195.1
[58] Field of Search ........................................... 424/195.1

[56] References Cited

U.S. PATENT DOCUMENTS

| | | |
|---|---|---|
| 4,501,734 | 2/1985 | Tanaka .................... 514/198 |
| 4,613,591 | 9/1986 | Aburada ..................... 514/34 |
| 4,618,495 | 10/1986 | Okuda .................. 424/195.1 |

FOREIGN PATENT DOCUMENTS

| | | |
|---|---|---|
| 90116873 | 10/1992 | European Pat. Off. . |
| 0091109 | 8/1978 | Japan . |
| 0046817 | 4/1981 | Japan . |
| 0188820 | 11/1983 | Japan . |
| 1109733 | 5/1986 | Japan . |
| 1112027 | 5/1986 | Japan . |
| 112027 | 5/1986 | Japan . |

OTHER PUBLICATIONS

Kim et al., "Anti–tumor effects of extracts of *Pulsatilla koreanan*(SB–31) in vitro," Proceedings of the American Association for Cancer Research, vol. 35, p. 408 (Mar. 1994).

S. Kim, "A Mechanistic Study of SB–31 (Extract of *Pulsatilla korean*): A Preliminary Report" (Apr. 1995).

S. Kim and S.B. Kim, "Anti–tumor effects of extracts of *Pulsatilla koreana* (SB–31) in vitro," Journal of Korean Cancer Association, vol. 26, No. 6, pp. 959–963 (1994).

*Primary Examiner*—Gollamudi S. Kishore
*Attorney, Agent, or Firm*—Birch, Stewart, Kolasch & Birch, LLP

[57] ABSTRACT

A pharmaceutical composition for treating tumor-bearing patients consisting essentially of a powder or an extract of a crude preparation of Pulsatilla Radix and Clematidis Radix, and at least one powdered or extracted ingredient selected from the group consisting of Ulmaceae Radix, Armeniacae Semen, Ginseng Radix, and Glycyrrhizae Radix.

5 Claims, 3 Drawing Sheets

PHARMACEUTICAL COMPOSITION HAVING AN ANTITUMOR ACTIVITY AND A PROCESS FOR PREPARATION THEREOF

This application is a continuation, of application Ser. No. 08/150,538 filed on Nov. 10, 1993, now abandoned, which is a continuation of application Ser. No. 07/867,076 filed on Apr. 14, 1992, now abandoned, which is a continuation of application Ser. No. 07/577,010 filed on Sep. 4, 1990, now abandoned.

BACKGROUND OF THE INVENTION

1. Field of the Invention

The present invention relates to a novel pharmaceutical composition having an antitumor activity comprising plant substances as main ingredients and a method of its manufacture. More particularly, the present invention relates to a antitumor composition utilizing extracts or powder of natural substances obtained from a combination of the genera Pulsatilla Radix and/or Clematidis Radix, and for further increasing the antitumor activity, at least one ingredient selected from the group consisting of Ulmaceae Bark, Armeniacae Semen, Ginseng Radix, and Glycyrrhizae Radix.

2. Description of the Prior Art

The genera Pulsatilla radix are grown all over the world. Pulsatilla Radix has been used as an antiphlogistic agent, astringent, hemostatic, and an agent for dysentery. It is known that the Pulsatilla Radix contains anemonin, protoanemonin, and saponin. Anemonin and protoanemonin have the following structures;

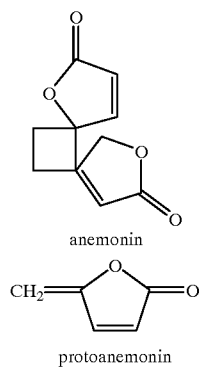

anemonin protoanemonin

Protoanemonin is the precursor for anemonin. Anemonin and protoanemonin are dissolved in water, alcohol, chloroform, and chlorinated ethylene. Until now, it has been never known that Pulsatilla Radix has an antitumor activity.

Clematidis Radix contains anemonin, anemonol, and saponin. It also has been used as an agent for gout, diuretic, and difficult menstruum in the Chinese medicine art. But until now, it is not known that the Clematidis Radix has an antitumor activity. The Ulmaceae Bark has mucin and tannin. Other ingredients than mucin and tannin are not known. It has been used as an agent for lenitive and binders in the Chinese medicine art. But it has been never used as an anti-tumor agent.

Armeniacae Semen contains amygdalin, oil, and emulsin and has been used as an agent for cough remedy, ointment, or solvent. But until now, it has been never used as an agent for antitumor.

Ginseng Radix has been known as a marvelous medicine in a Chinese medicine art. It has been used as a tonic, an agent for acute gastritis, and an agent for various bleeding diseases. In recent years, it is reported that Ginseng Radix has an anticarcinogenic effect. In Ginseng Radix, ginseng saponin, essence oil, panaxtriol, beta-sisterol etc. are contained.

Glycyrrhizae Radix contains glycyrrhizin, liquiritin, licoricidin, and liquiritoside and has been used as an agent for cough remedy, expectorant, diaphoretic, and gastritis. But, it is recently known that the Glycyrrhizae Radix has an anti-tumor activity.

SUMMARY OF THE INVENTION

Accordingly, it is an object of the present invention to provide an antitumor composition of plant substances which is not harmful to human body and excellent remedy effect for antitumor.

Another object of the present invention is to provide s pharmaceutical composition utilizing extracts or powders of Pulsatilla Radix and/or Clematidis Radix.

A further object of the present invention is to provide a pharmaceutical composition comprising Pulsatilla Radix and/or Clematidis Radix, and one or more natural substances selected from the group consisting of Ulmaceae Bark, Armeniacae Semen, Ginseng Radix, and Glycyrrhizae Radix wherein the Ulmaceae Bark, Armeniacae Semen, Ginseng Radix, and Glycyrrhizae Radix are added to Pulsatilla Radix and/or Clematidis Radix in the form of powder or extract, the anti-tumor activity is much more strengthened.

Still another object of the present invention is to provide a method for the preparation of pharmaceutical composition having an antitumor activity from the above-identified natural substances.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a novel pharmaceutical composition utilizing extracts and powders of natural substances obtained from a combination of the genera Pulsatilla Radix and/or Clematidis Radix, and optionally at least one ingredient selected from the group consisting Ulmaceae Bark, Armeniacae Semen, Panax Ginseng, and Glycyrrhizae Radix.

BRIEF DESCRIPTION OF THE DRAWINGS

The present invention will become more fully understood from the detailed description given hereinbelow and the accompanying drawing which are given by way of illustration only, and thus are not limitative of the present invention, and wherein.

DESCRIPTION OF THE PREFERRED EMBODIMENTS

Figure 1:
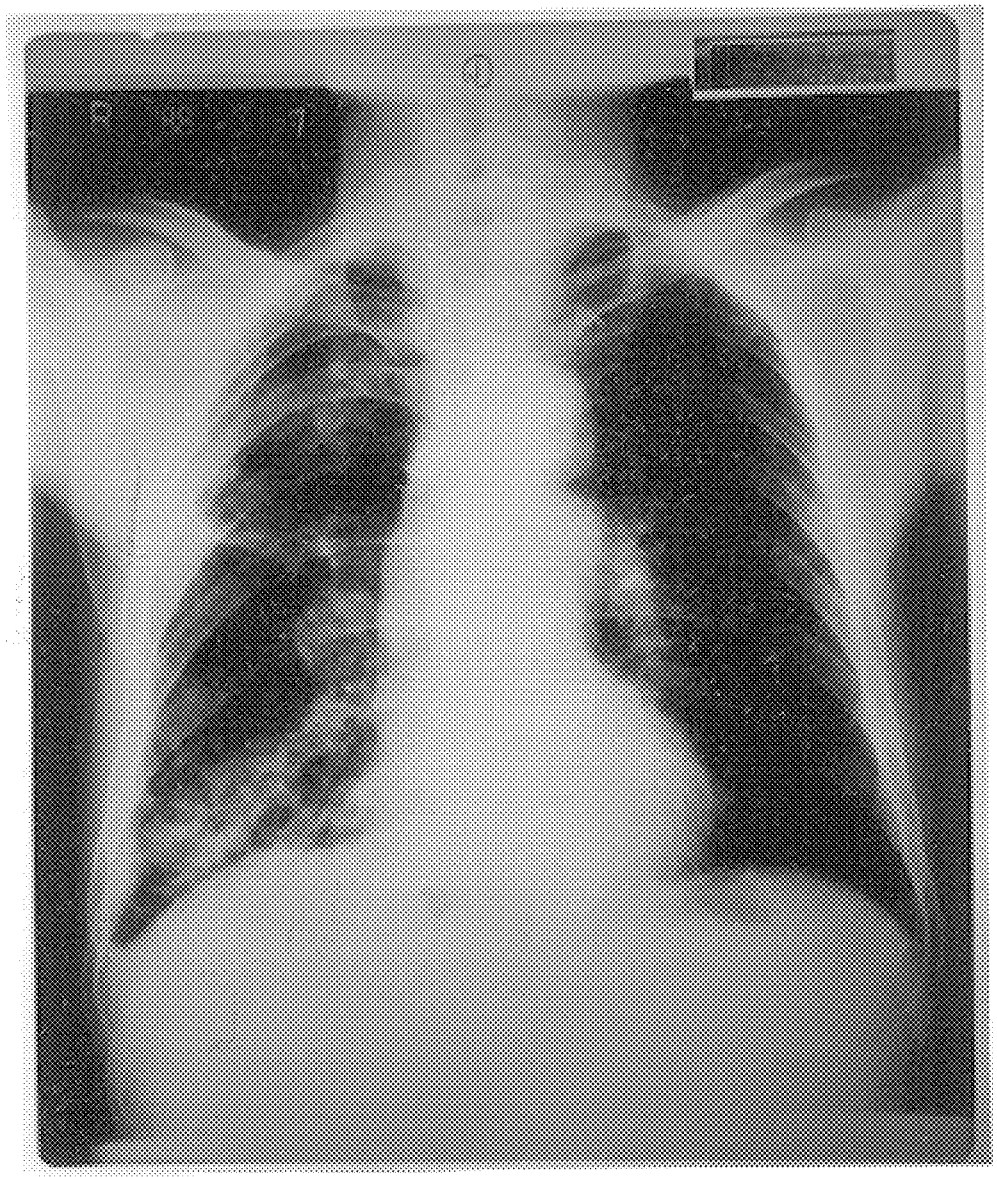
FIG. 1 is an x-ray chart taken before the medication of the composition of the Example 7 according to the present invention.

The present invention pertains an antitumor effective natural substance composition which utilizes a powder and an extract which is a mixture of Pulsatilla Koreana Nakai, Pulsatilla Cernua, *Pulsatilla davurica*, or *Pulsatilla ratinsis* or Pulsatilla Radix, and/or *Clematidis mandshurica* Maximowicz of Clematidis Radix.

In another embodiment of the present invention, at least one natural substance selected from the group consisting of *Ulmus davidiana* var. *japanica* of Ulmacae Bark, *Prunus armenicaca* Linne var. ansu Maximowicz of *Armenicae Semen*, Panax Sclinseng Nees of Ginseng Radix, and *Glycyrrhiza glabra* Linne var. *grandifera* of Glycyrrhizae Radix is added to the initial mixture of natural substances, the antitumor composition obtained therefrom is particularly effective in the antitumor remedy.

The antitumor natural substance composition of the present invention comprises 0–10 parts by weight of Pulsatilla Radix, 0–10 parts by weight of Clematidis Radix (However, Pulsatilla Radix and Clematidis Radix are not zero at the same time), 0–5 parts by weight of Ginseng Radix, 0–5 parts by weight of Ulmaceae bark, 0–3 parts by weight of *Armeniacae Semen*, and 0–5 parts by weight of Glycyrrhizae Radix based on the air-dry. They can be used in the form of powder or extract extracted by conventional solvent. One or more diluents selected from the group consisting of conventional carriers, antioxidants, preservatives, dissolving agents, disintegrators, lubricants binders, and solvents may be added to the above ingredients. The natural substances of the present invention are air-dried and finely ground or extracted by water, lower alcohol, chloroform, methylenechloride, or any other solvent which can extract active substances from the natural substances at the temperature of from 0° C. to the boiling point of the solvent for from 30 minutes to 24 hours. The solvent from the extract solution may be distilled off to obtain extract. The extract may be dissolved in water, ethylalcohol, or mixture thereof. When water is used as a solvent, the solution may be directly used as a pharmaceutical preparation without distillation of water.

When each of the ingredients is used in the extract form, each of the natural substances may be extracted separately or 2 kinds of the natural substances, or more may be combined and extracted at the same time to obtain the extract. To the powder or extract of natural substances, the following diluents may be added. They are carriers such as lactose, various starches, sucrose, mannitol, sorbitol, calcium sulfate, aluminum silicate, calcium sulfate, calcium carbonate; binders such as sucrose, glucose, starch paste, gelatin, carboxymethylcellulose, methylcellulose, gum arabic, gum tragacanth, ethylcellulose, sodium alginate, hydroxypropylmethylcellulose, polyvinylpyrrolidone, soluble cellulose; disintegrators such as starch, carboxymethylcellulose, methylcellulose, crystalline cellulose; lubricating agents such as magnesium stearate, calcium stearate; wetting agents such as glycerine, propylene glycol and sorbitol; preservatives such as sodium benzoate, methyl p-hydroxybenzoate, propyl p-hydroxybenzoate, benzalkonium chloride, chlorobutanol, sodium dehydroacetate, polymyxin B sulfate; dissolving agents such as soluble alcohols and derivatives thereof, various surfactants; antioxidants such as sodium sulfite, sodium pyrosulfate, sodium metabisulfate, sodium bisulfite, rongalite, ascorbic acid; isotonic agents such as sodium chloride, dextrose; indolent agent such as benzylalcohol and chlorobutanol; and ointment base such as vaseline, fluid paraffin plastibase and various silicones, lard, various vegetable oils, waxes, refined lanolin.

The pharmaceutical composition of the present invention can be prepared in the forms of powder, tablets, capsule, syrup, suspension, oral solution or solution for injection, ointment, or any other pharmaceutical preparation conventionally used in the pharmaceutical industry.

About 0.5–10 g of the Pulsatilla Radix and/or the Clematidis Radix in the form of powder or extract which is extracted from 0.5–10 g of the Pulsatilla Radix and/or the Clematidis Radix may be administered for 1–10 times a day.

The present invention will now be described in more detail in connection with the following examples which should be considered as being exemplary and not limiting the present invention.

EXAMPLE 1

4 g of air-dried Pulsatilla Radix, 2 g of air-dried Ulmus Bark and 1 g of air-dried Glycyrrhizae Radix were finely ground, mixed uniformly, and divided into each 1.5 g of the mixture in vinylcoated envelope and sealed.

EXAMPLE 2

4 g of air-dried Pulsatilla Radix, 2 g of air-dried Clematidis Radix, 2 g of air-dried Ginseng Radix, and 2 g of Glycyrrhizae Radix were finely ground, mixed uniformly and divided into each 1.5 g of the mixture in vinyl coated envelope and sealed.

EXAMPLE 3

6.26 g of air-dried Pulsatilla Radix were added to 90 ml of purified water. The mixture was warmed at the temperature of 60° C. and stirred for 60 minutes. The mixture was centrifuged at 3,500 r.p.m. for about 30 minutes. About 60 ml of the separated solution was sterile-filtered in a sterilization room at a temperature of 60° C. or below. The solution was made into isotonic solution by adding a suitable amount of NaCl. The isotonic solution were sterile-filtered once again and divided to each 2.5 ml of the solution in an ampoule of 3 ml at the sterile state and sealed to obtain an injection ampoule.

EXAMPLE 4

4 g of air-dried and powdered Pulsatilla Radix, 2 g of air-dried powdered Ulmus Bark, 2 g of air-dried and powdered Ginseng Radix, and 1 g of air-dried and powdered Glycyrrhizae Radix were added to 90 ml of purified water. The mixture was stirred for 60 minutes at a temperature of about 80° C. by adding purified water corresponding to the water distilled off. The mixture was cooled at a room temperature, centrifuged with 3,500 r.p.m. for about 30 minutes to obtain about 46 ml of solution. To the solution was added NaCl to obtain an isotonic solution. The isotonic solution was filtered with a conventional filtration method in a sterile room, sterile-filtered and divided into each 2 ml of the solution in ampoule of 3 ml, sealed and stored in refrigerator.

EXAMPLE 5

62.6 g of air-dried and powdered Pulsatilla Radix, 31.3 g of air-dried and powdered Ginseng Radix, 10 g of air-dried and powdered Glycyrrhizae Radix were added to 900 ml of purified water. The mixture was stirred for 60 minutes at about 60° C. by adding purified water corresponding to the water distilled off. The mixture was filtered and the filtrate was concentrated to obtain about 26.4 g of the extract.

EXAMPLE 6

6 g of air-dried and powdered Clematidis Radix, 3.13 g of air-dried and powdered Ginseng Radix, 2 g of *Armemiacae*

*Semen*, and 1 g of air-dried and powdered Glycyrrhizae Radix were added to 90 ml of 40% (v/v) ethylalcohol and the mixture was stirred for about 120 minutes at about 40° C. and extracted. The mixture was centrifuged with 3,500 r.p.m. to obtain about 40 ml of solution. The solution was concentrated to obtain about 2.50 g of extract.

EXAMPLE 7

| | |
|---|---|
| Extract obtained in the Example 5 | 130 mg |
| Sodium metabisulfite | 3.0 mg |
| Methylparaben | 0.8 mg |
| Propylparaben | 0.1 mg |
| Isotonic solution | qs to be 2 ml of the total volume |

The mixture solution was filled into 2 ml of ampoule by the conventional method.

EXAMPLE 8

| | |
|---|---|
| Extract obtained in the Example 5 | 200 mg |
| Crystalline cellulose | 50 mg |
| Hydroxypropylcellulose | 17 mg |
| Magnesium stearate | 3 mg |

270 mg of tablet was obtained by the conventional method.

EXAMPLE 9

| | |
|---|---|
| Extract obtained in the Example 5 | 200 mg |
| Talc | 10 mg |
| Colloid silica | 5 mg |
| Lactose | 85 mg |

300 mg of hard capsule was obtained by the conventional method.

EXAMPLE 10

| | |
|---|---|
| Extract obtained in the Example 5 | 1000 mg |
| Sucrose | 2000 mg |
| Methylparaben | 20 mg |
| Propylparaben | 5 mg |
| Glycerine | 20 mg |
| Sodium saccharin | 10 mg |
| Orange essence | qs |
| Purified water | qs to be 100 ml of the total volume |

Oral solution was obtained by the conventional method.

EXAMPLE 11

| | |
|---|---|
| Extract obtained in the Example 6 | 1.5 mg |
| Gum tragacanth | 1.0 mg |
| Glycerine | 2 ml |
| Purified water, | qs to be 50 ml of the total volume |

Oral solution was obtained by conventional method.

Experiment 1

Acute toxicity

Animals: dd mice of body weight of 20–25 g were used.

Method: The samples prepared in the Example 3 were administered through p.o., s.c., and i.v. respectively, and the animals were watched for 72 hours whether the animals were dead or not.

Experiment 2

Acute toxicity

Animals: Sprague-Dawley rats of body weight of 120–130 g were used.

Method: The samples prepared in the Example 3 were administered through p.o., s.c., and i.v. respectively, and the animals were watched for 72 hours whether the animals were dead or not.

Results: The results of these experiments were shown in the Table I and II.

Table I

Acute Toxicity of the composition in mice of the present invention

| | Sample Dose | | No. of Animals | | MLD | | $LD_{50}$ | |
|---|---|---|---|---|---|---|---|---|
| Route | ml/20 | ml/kg | dosed | died | ml/20 g | ml/kg | ml/20 g | ml/kg |
| P.O. | 1.0 | 50 | 10 | 0 | >1.0 | >50 | — | |
| | 0.4 | 20 | 10 | 0 | | | | |
| S.C. | 0.8 | 40 | 10 | 0 | >0.8 | >40 | — | |
| | 0.4 | 20 | 10 | 0 | | | | |
| i.v. | 0.19 | 9.5 | 6 | 0 | | | | |
| | 0.22 | 11.0 | 6 | 1 | | | | |
| | 0.25 | 12.5 | 6 | 2 | — | | | |
| | 0.28 | 14.0 | 6 | 4 | | | | |
| | 0.30 | 15.0 | 6 | 6 | | | | |

$LD_{50}$ value was calculated by the Behren's method.

Table II

Acute Toxicity of Sample P in Rats

| | Sample Dose | | No. of Animals | | MLD | | $LD_{50}$ | |
|---|---|---|---|---|---|---|---|---|
| Route | ml/20 | ml/kg | dosed | died | ml/20 g | ml/kg | ml/20 kg | ml/kg |
| P.O. | 4.0 | 20 | 8 | 0 | 4.0 | 20 | — | |
| S.C. | 4.0 | 20 | 8 | 3 | 4.0 | 20 | — | |
| | 3.0 | 15 | 5 | 0 | | | | | wherein the Table I and II, the pharmaceutical composition of the present invention has very weak acute toxicity.

Experiment 3

Antitumor effect against Sarcoma 180

Animals: dd mice (male) of body weight of 20–25 g were used.

Method: Sarcoma 180 tumor cells of $5 \times 10^6$ were injected in the test mice. after 7 days, samples of 0.3 ml of the composition of the Example 3 according to the present invention were injected (s.C.) for 5 days. The animals were sacrificed after 30 days and the tumors were taken out and weighed. Additionally, the appearance of the tumor size was observed on the 10th day and 20th day, respectively, after the starting date of the administration of the composition of the present invention. 5–10 mice were used for each group.

Results: the results were shown in the Tables III and IV.

Table III

Antitumor effect of the present composition against Sarcoma 180 implanted S.C. in mice

| Material | Dose ml/20 g, S.C. | Tumor size (min in diameter) | Tumor wt. (g) | T/C (%) | Complete regression |
|---|---|---|---|---|---|
| Saline | 0.3 × 5d | 18.6 ± 2.2 | 2.71 ± 0.87 | — | 10/10 |
| Composition of Example 3 | 0.3 × 5d | 4.2 ± 1.6 | 0.44 ± 0.09 | 16.1 | 0/7 |

Table IV

Antitumor effect of the present composition against Sarwma 180 implanted S.C. in mice

| Material | Dose ml/ 20 g, p.o. | Tumor size (mm) 10th day | Tumor size (mm) 20th day | Tumor wt (g) 30th day | T/C (%) | Complete regression |
|---|---|---|---|---|---|---|
| Saline | 0.4 | 6.3 ± 0.86 | 17.2 ± 1.03 | 5.64 ± 1.1 | — | 0/9 |
| Composition of Example 3 | 0.4 | 4.83 ± 0.83 | 12.4 ± 0.92 | 3.69 ± 0.76 | 65% | 0/5 | wherein the data were obtained 20 days after the administration of the test materials.

The mean tumor weight of the control group was 2.71 g but the mean tumor weight of the injected group of the composition of the present invention was 0.44 g. According to the regulation of Cancer Institute of U.S.A., when the T/C (%) of any test compound is 42% or below, the compound is determined to be effective. As the T/C (%) of the composition of the present invention is 16.1%, the composition of the present invention has an excellent effect against Sarcoma 180.

Experiment 4

Clinical Test on volunteer

Tested Person: Mr. Hyun Suck SUH aged 18 (Address: Majungri, Nam-Myun, Buye-Kun, Chungnam-Do, Republic of Korea)

Kind of disease: Tumors of the lymph node on neck.

Diagnosis: At the Chungnam Medical College Hospital on Jul. 17, 1973.

Period of medication: From Sep. 20, 1973 to Mar. 5, 1974.

Method of medication: The composition prepared by the Example 3 according to the present invention was injected subcutaneously 2 ml once a day for 1 month. Thereafter, the composition of the present invention was injected subcutaneously 4 ml twice a day. After 2 months and 10 days from the start of medication, the tumors disappeared. Thereafter, the medication was continued for 3 months and 5 days.

After 3 years from the end of medication, the Chungnam Medical College Hospital decided that the patient was completely cured.

Experiment 5

Clinical Test on volunteer

Tested person: Mr. Keun Bae LEE aged 66 (Address: 793, Chungan-3-Dong, Danbuk-Myun, Euisung-Kun, Kyungsangbuk-Do, Republic of Korea)

Kind of Disease: Lung Cancer

Diagnosis: Dong San Hospital of Kyemyung University on Sep. 29, 1987.

Period of medication: From Apr. 8, 1988 to Nov. 23, 1988 for 7 months and 15 days.

Figure 2:
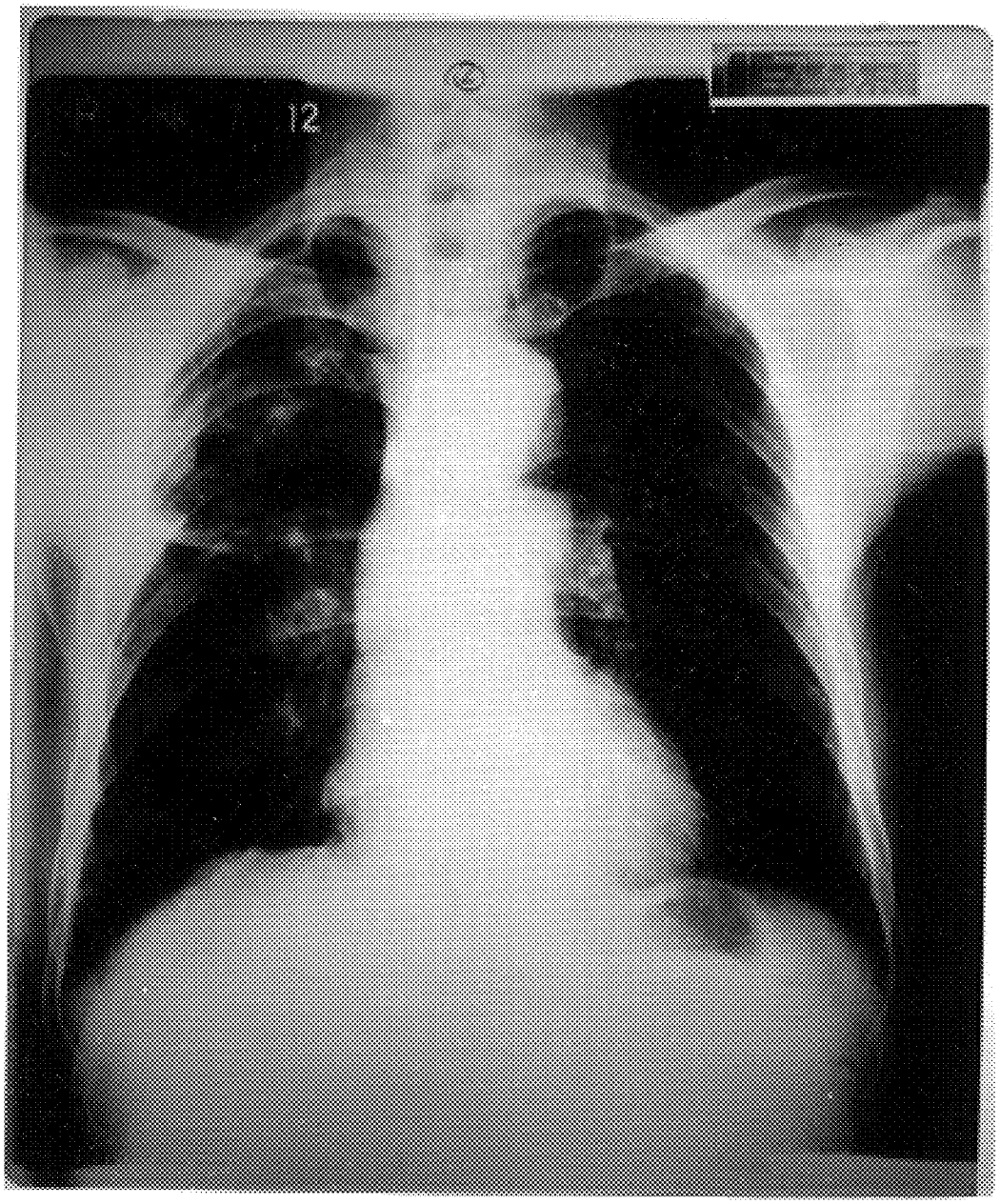
FIG. 2 is an x-ray chart taken after 3 months the medication of the Example 7 according to the present invention.
Figure 3:
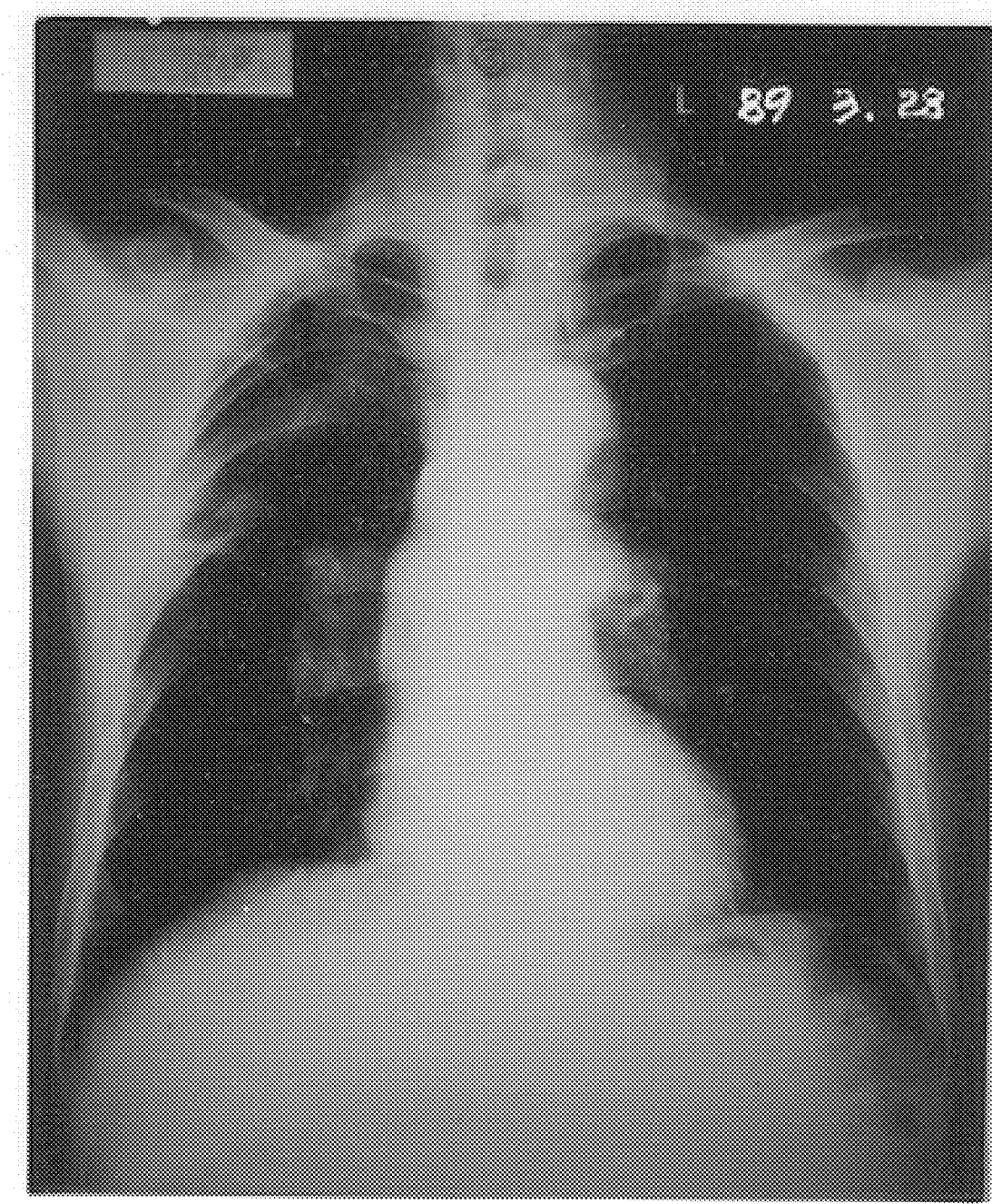
FIG. 3 is an x-ray chart showing that the composition of the present invention has an excellent effect against lung cancer.

Method of medication: The present composition prepared by the Example 7 according to the present invention was injected subcutaneously 2 ml once a day. Dong San Hospital reported that tumors disappeared on Dec. 5, 1988 as shown in FIG. 1 showing an X-ray chart taken before the medication of the composition of the present invention, FIG. 2 showing an X-ray chart taken after 3 months the medication of the present composition thereof, and FIG. 3 showing X-ray chart taken after the end of the medication of the composition thereof.

As shown the X-ray charts showing that the composition of the present invention has an excellent effect against lung cancer.

Experiment 6

Clinical Test on volunteer

Tested person: MR. No Charn PARK aged 63 (Address: 196, Sukwan-Ri, Nami-Myun, Chungwon-Kun, Chungchungbuk-Do, Republic of Korea).

Kind of disease: Progressed stomach cancer.

Diagnosis: Chungnam Medical College Hospital on Mar. 15, 1988.

Period of medication: From Apr. 8, 1988 to Apr. 30, 1989 for 12 months and 22 day.

Method of medication: The composition prepared by the Example 3 according to the present invention was injected (i.m.) 2 ml once a day, injected (i.v.) 2 ml once a day, and administered orally 2.2 ml once a day simultaneously. After one month of the medication, about 20% of improvement effect was obtained. After 3 months of the medication, about 30% of improvement effect was obtained. Thereafter, no improvement effect or ingravescence effect appeared till 5th month of medication. Thereafter, the injections were maintained and the oral doses was doubled. About 80% of clinical effect of the improvement was obtained at 6th month. After 9th month of medication, all tumors disappeared. From 10th month, only 2 ml of the composition of the present invention once a day was injected (i.v.). Daejeon Chungang X-ray Clinic decided on Mar. 25, 1989 that the patient was completely recovered.

Experiment 7

Clinical Test on volunteer

Tested person: Mr. Duck Sang KIM aged 46 (Address: 90–20 Sajik-2-Dong, Dongrae-Ku, Pusan, Republic of Korea).

Kind of Disease: Progressed stomach cancer.

Diagnosis: Pusan Inje Medical College attached Baik Hospital on Mar. 8, 1988.

Period of medication: From Mar. 3, 1988 to Feb. 3, 1989 for 10 months.

Method of medication: The composition prepared by the Example 7 according to the present invention was injected (i.m.) 2 ml once a day from Apr. 3, 1988. A little amount of the composition of the present invention was orally administered simultaneously. From 20 days of the medication, the injection method (i.m.) was changed into i.v. injection. After 3 months of medication, about 30% of the improvement effect was obtained. After 5 months of the medication, about 80% of the improvement effect was obtained. From 6th month of medication, the amount of oral administration was doubled. After 8 months of the medication, no tumors appeared. Injection was ended from the 10th month of medication and only the oral administration was continued for one month. Baik Hospital of Pusan Inje Medical College decided that the patient was completely recovered.

As shown in the Experiments above, the pharmaceutical composition of the present invention has an excellent anti-tumor activity.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A pharmaceutical composition for treatment of a tumor, comprising a mixture of a first component consisting of a dried aqueous extract of Pulsatilla Radix and a second component consisting of an aqueous extract of at least one plant selected from the group consisting of Clematidis Radix, Ulmaceae bark, *Armeniacae semen*, Ginsenc Radix and Glycyrrhizae Radix, wherein each component is provided in an amount effective for the treatment of a tumor, and further wherein said dried aqueous extract of Pulsatilla Radix is present at 18% to 63% w/w in the composition.

2. The composition of claim 1, wherein Pulsatilla Radix, Ulmaceae bark, Ginseng Radix and Glycyrrhizae Radix are present in a ratio of 4:2:2:1 dry weight before extraction.

3. The composition of claim 1, wherein Pulsatilla Radix, Ginseng Radix and Glycyrrhizae Radix are present in a ratio of 6:3:1 dry weight before extraction.

4. A pharmaceutical composition for treatment of a tumor, comprising an aqueous extract of a mixture of a first component consisting of a dried, powdered Pulsatilla Radix and a second component consisting of at least one dried, powdered ingredient selected from the group consisting of Clematidis Radix, Ulmaceae bark, *Armeniacae semen*, Ginseng Radix and Glvcvrrhizae Radix, wherein each component is provided in an amount effective for the treatment of a tumor, and further wherein said first component is present at 18% to 63% w/w of the mixture that is extracted.

5. The pharmaceutical composition according to claim 1, wherein said tumor is sarcoma.

* * * * *